(12) United States Patent
Akitsu et al.

(10) Patent No.: US 8,945,526 B2
(45) Date of Patent: Feb. 3, 2015

(54) AMPHIPHILIC SUBSTANCE, AND DRUG DELIVERY SYSTEM AND MOLECULAR IMAGING SYSTEM USING THE SAME

(75) Inventors: Hitoshi Akitsu, Kyoto (JP); Eiichi Ozeki, Kyoto (JP); Ryoji Fushimi, Kyoto (JP); Shunsaku Kimura, Kyoto (JP); Masashi Isozaki, Kanagawa (JP); Shigenori Nozawa, Kanagawa (JP)

(73) Assignees: Shimadzu Corporation, Kyoto (JP); Kyoto University, Kyoto (JP)

( * ) Notice: Subject to any disclaimer, the term of this patent is extended or adjusted under 35 U.S.C. 154(b) by 2080 days.

(21) Appl. No.: 11/812,131

(22) Filed: Jun. 15, 2007

(65) Prior Publication Data
US 2008/0019908 A1 Jan. 24, 2008

(30) Foreign Application Priority Data

Jul. 20, 2006 (JP) ................................. 2006-198790

(51) Int. Cl.
| | | |
|---|---|---|
| *A61K 31/74* | (2006.01) | |
| *C08G 69/10* | (2006.01) | |
| *A61K 49/00* | (2006.01) | |
| *B82Y 5/00* | (2011.01) | |

(52) U.S. Cl.
CPC ............ *C08G 69/10* (2013.01); *A61K 49/0034* (2013.01); *A61K 49/0043* (2013.01); *A61K 49/0052* (2013.01); *A61K 49/0093* (2013.01); *B82Y 5/00* (2013.01)
USPC ..................................................... 424/78.08

(58) Field of Classification Search
None
See application file for complete search history.

(56) References Cited

U.S. PATENT DOCUMENTS

| 5,013,556 A | 5/1991 | Woodle et al. |
| 5,051,351 A | 9/1991 | Tabor et al. |
| 2002/0132254 A1* | 9/2002 | Twu .................................. 435/6 |
| 2004/0254352 A1 | 12/2004 | Metselaar et al. |

FOREIGN PATENT DOCUMENTS

| FR | 2533222 A | * 3/1984 |
| JP | 3-37271 A | 2/1991 |
| JP | 8-134160 A | 5/1996 |
| JP | 2004-527585 A | 9/2004 |
| JP | 2005-172522 A | 6/2005 |
| JP | 2005-220045 A | 8/2005 |

OTHER PUBLICATIONS

English Translation of Douy, FR 2533222.*

(Continued)

*Primary Examiner* — Paul Dickinson
(74) *Attorney, Agent, or Firm* — Cheng Law Group, PLLC

(57) ABSTRACT

The present invention provides a novel amphiphilic substance, a nanoparticle using the novel amphiphilic substance, which can be used as a nanocarrier having high biocompatibility, a drug delivery system and a probe useful for the system, and, a molecular imaging system and a probe useful for the system. An amphiphilic block polymer comprising a hydrophilic block; and a hydrophobic block, wherein the hydrophilic block is a hydrophilic polypeptide chain having 10 or more sarcosine units, and the hydrophobic block is a hydrophobic molecular chain comprising units selected from the group consisting of amino acid units and hydroxyl acid units as essential structural units, and having 5 or more of the essential structural units.

17 Claims, 5 Drawing Sheets
(2 of 5 Drawing Sheet(s) Filed in Color)

(56) References Cited

OTHER PUBLICATIONS

Douy, A. et al., "Amphipathic block copolymer . . . ", 1987, Polymer. 28, pp. 147-154.*

Kidchob, T., et al., "Preparation, structure and release profile of polypeptide microcapsules", 1995, J. Contr. Release, 40, pp. 285-291.*

Jeong, J.H., et al., "Poly(L-lysin)-g-poly(D,L-lactic-co-glycolic acid) micelles", 2002, J. Contr. Release, 82, pp. 159-166.*

Liang, H., et al., "Preparation of nanoparticles composed of poly(γ-glutamic acid)-poly(lactide) block copolymers", 2005, J. Contr. Release, 105, pp. 213-225.*

Tongjit Kidchob et al., "Thermoresponsive release from poly(Glu(OMe))-*block*-poly (Sar) microcapsules with surface-grafting of poly(*N*-isopropylacrylamide)", Journal of Controlled Release 50, 1998, pp. 205-214, Elsevier Science B.V. (10 pages).

Tongjit Kidchob et al., "Amphiphilic poly(Ala)-*b*-poly(Sar) microspheres loaded with hydrophobic drug", Journal of Controlled Release 51, 1998, pp. 241-248, Elsevier Science B.V. (8 pages).

Janos Szebeni et al., The Role of Complement Activation in Hypersensitivity to Pegylated Liposomal Doxorubicin (Doxil®), Journal of Liposome Research, 10(04), pp. 467-481, 2000, Marcel Dekker, Inc. (15 pages).

Ande Bao et al., "Direct $^{99m}$Tc Labeling of Pegylated Liposomal Doxorubicin (Doxil) for Pharmacokinetic and Non-Invasive Imaging Studies", The Journal of Pharmacology and Experimental Therapeutics, 2004, pp. 419-425, vol. 308, No. 2, USA (7 pages).

Hiroyuki Nishikawa et al., "Formation of gold nanoparticles in micoreactor composed of helical peptide assembly in water", Journal of Colloid and Interface Science 280, pp. 506-510, 2004, Elsevier, Inc. (5 pages).

Eric P. Holowka et al., "Charged Polypeptide Vesicles with Controllable Diameter", JACS Articles, Aug. 16, 2005, pp. 12423-12428, vol. 127, No. 35, Published on the Web, J. Am. Chem. Soc. (6 pages).

JPO Submission of Certificate of Exceptions to Lack of Novelty (and translation), Aug. 18, 2006, Related to Japanese App. No. 2006-198790, (46 pages with translation).

Notification of Reasons for Refusal for the Application No. 2006-198790 from Japan Patent Office mailed Nov. 15, 2011.

\* cited by examiner

US 8,945,526 B2

AMPHIPHILIC SUBSTANCE, AND DRUG DELIVERY SYSTEM AND MOLECULAR IMAGING SYSTEM USING THE SAME

BACKGROUND OF THE INVENTION

1. Field of the Invention

The present invention relates to a novel amphiphilic substance, and a drug delivery system and a molecular imaging system using the novel amphiphilic substance.

2. Disclosure of the Related Art

As described in Japanese Unexamined Patent Publication No. 2005-172522, in recent years, there has been a growing interest in nanotechnology, and new functional materials utilizing the characteristics inherent in nanosized substances have been developed. These new functional materials can be used in various fields such as energy, electronics, and medical and pharmaceutical fields. Among such various fields, nanotechnology is attracting attention in the field of detection of substances in biological samples and in-vivo imaging. Particularly, in the medical and pharmaceutical field, liposomes and the like which are nanoparticles composed of phospholipid are used as carriers for drug delivery system (DDS).

As described in Japanese Unexamined Patent Publication No. 2005-220045, in the medical and pharmaceutical field, it is desired that changes in the form and function of organs or tissues caused by diseases in a living body are promptly and accurately detected by a simple method at early stages of the diseases to early diagnose and treat the diseases. Particularly, in order to early diagnose and treat cancer, it is essential to detect a small diseased part and to determine the size of the diseased part at its early stage. Examples of a method for early diagnosis include endoscopic examination and diagnostic imaging such as X-ray imaging, MRI, and ultrasonic imaging. In a case where a radioactive indicator is used, the lifetime of the indicator is limited due to its half-life. In addition, in this case, a diagnostic apparatus is very expensive.

On the other hand, diagnostic imaging can also be carried out using a fluorescence indicator or a near-infrared indicator. Such a diagnosis method does not impose strict limitations on its indicator's own lifetime, and a diagnostic apparatus for this method is not very expensive as compared to a radiodiagnostic apparatus. In addition, such optical diagnosis is non-invasive to a living body. For example, autofluorescence observation via endoscope is in practical use, which utilizes the fact that the autofluorescence of tumor cells is weaker than that of normal cells (excitation: 450 nm, emission: 520 nm).

As a near-infrared diagnosis method, near-infrared fluorescence imaging, in which a near-infrared fluorochrome is allowed to accumulate in a tumor region thereby enabling imaging of the tumor region, is also attracting attention. In this method, a compound that can emit fluorescence in the near-infrared region by irradiation with excitation light is administered as a contrast agent into a living body, and then the body is externally irradiated with excitation light having a near-infrared wavelength to detect fluorescence emitted from the fluorescent contrast agent accumulating in a tumor region. In this way, a diseased region is determined. As such a contrast agent, a nanoparticle, such as a liposome, having an indocyanine green derivative encapsulated therein has been proposed (see Japanese Unexamined Patent Publication No. 2005-220045).

On the other hand, peptide nanoparticles having higher biocompatibility have also been known (see Journal of Controlled Release 50 (1998) 205-214, Journal of Controlled Release 51 (1998) 241-248, Journal of Colloid Interface Science 280 (2004) 506-510, and Journal of American Chemical Society 2005, 127, 12423-12428).

SUMMARY OF THE INVENTION

Endoscopic examination and diagnostic imaging such as X-ray imaging, MRI, and ultrasonic imaging have their respective advantages, but they are invasive methods imposing psychological pressure, pain, or exposure to radiation on subjects. Further, in a case where a radioactive indicator is used, the lifetime of the indicator is limited due to its half-life. In addition, in this case, a diagnostic apparatus is very expensive.

On the other hand, in a case where a fluorescence indicator or a near-infrared indicator is used, there is a barrier that only the information about a very shallow region near the surface of a living body is obtained because a large amount of hemoglobin showing absorption in the visible light region is present in a living body. However, in the near-infrared region (700 to 1300 nm), although substituent groups having a hydrogen bond show absorption, the absorption is relatively small, and therefore near-infrared rays are likely to pass through living tissues. From the fact, it can be considered that utilization of such characteristics of near-infrared rays makes it possible to obtain information about the inside of a living body without applying an unnecessary load to the body. Further, there is a possibility that near-infrared fluorescence imaging gives very useful information about a subject when the subject is limited to a small animal or a region near the body surface.

The liposome disclosed in Japanese Unexamined Patent Publication No. 2005-220045 is recognized by immune system cells, such as macrophages, in the blood and eliminated, and is therefore captured by a reticular system (RES), such as liver and spleen, containing a large amount of macrophage-like cells. For this reason, the liposome is not properly retained in the blood. There is proposed a liposome coated with polyethylene glycol (PEG) to improve its retention in the blood (see U.S. Pat. No. 5,013,556). It is believed that the PEG of the liposome has the function of improving the hydrophilicity of the liposome surface to prevent the liposome from being recognized as foreign matter by an immune system such as RES. However, there is no detailed report about the safety of such a PEG-coated liposome and its metabolite in a living body. In addition, there is a report that a commercially available PEG-coated liposome, that is, Doxil® causes anaphylactoid reaction relatively frequently when administered to humans (see Journal of Liposome Research, 10(4), 467-484 (2000)). Therefore, there is demand for development of nanoparticles having a higher degree of safety.

Further, there is no report about practical use of peptide nanoparticles as carriers for drug delivery, particularly for contrast agent delivery. Therefore, there is also demand for development of nanoparticles which have higher biocompatibility and higher degree of safety and which can be used as carriers for effectively delivering and accumulating a drug, particularly a contrast agent to and in a diseased part.

It is therefore an object of the present invention to provide a novel amphiphilic substance. Another object of the present invention is to provide a nanoparticle using the novel amphiphilic substance, which can be used as a nanocarrier having high biocompatibility. Still another object of the present invention is to provide a drug delivery system and a probe useful for the system, and a molecular imaging system and a probe useful for the system.

The present inventors have made intensive research, and as a result have found that an amphiphilic block polymer having, as a hydrophilic block, a peptide chain comprising 10 or more structural units derived from sarcosine (N-methylglycin) self-assembles to form nanoparticles and that the nanoparticles are stable in a biological system and can accumulate in a diseased part. These findings have led to the completion of the present invention.

The present invention includes the following.

The following (1) to (6) relate to an amphiphilic block polymer.

(1) An amphiphilic block polymer comprising:
a hydrophilic block; and
a hydrophobic block, wherein
the hydrophilic block is a hydrophilic polypeptide chain having 10 or more sarcosine units, and
the hydrophobic block is a hydrophobic molecular chain comprising units selected from the group consisting of amino acid units and hydroxyl acid units as essential structural units, and having 5 or more of the essential structural units.

In this specification, the term "amino acid" refers to natural amino acids, unnatural amino acids, and derivatives thereof obtained by modification and/or chemical alteration, and includes $\alpha$-, $\beta$-, and $\gamma$-amino acids.

(2) The amphiphilic block polymer according to the above (1), wherein
the hydrophobic molecular chain is selected from the group consisting of a hydrophobic polypeptide chain having 5 or more hydrophobic amino acid units, a hydrophobic polyester chain having 5 or more hydroxyl acid units, and a hydrophobic depsipeptide chain having a total of 5 or more of both amino acid units and hydroxyl acid units.

(3) The amphiphilic block polymer according to the above (1) or (2), further comprising a marker group selected from signal groups and ligands.

In the above (3), the term "signal group" refers to a group that can be detected for imaging, and includes fluorescent groups, radioactive element-containing groups, and magnetic groups.

In the above (3), the term "ligand" includes one for allowing molecular assemblies comprising the amphiphilic block polymer to specifically bind to a target region when the molecular assemblies are administered, and one which can coordinate to a molecule or an atom of a drug or a signal agent so that the drug or the signal agent can be delivered to a target region when the molecular assemblies are administered.

(4) The amphiphilic block polymer according to the above (3), wherein the marker group is bound to an end of the amphiphilic block polymer.

In the above (4) and the following (5), the term "bound" specifically refers to covalent bonding, and includes direct bonding to a specific part of the polymer and indirect bonding to a specific part of the polymer via an appropriate spacer group.

In the present invention, as described in the above (4), the marker group may be directly or indirectly bound to a terminal structural unit of the structural units constituting the amphiphilic block polymer molecule.

(5) The amphiphilic block polymer according to the above (3) or (4), wherein the marker group is bound to the unit constituting the amphiphilic block polymer.

In the present invention, as described in the above (5), the marker group may be directly or indirectly bound to at least an inner structural unit of both inner and terminal structural units constituting the amphiphilic block polymer molecule. That is, the marker group may be bound to a relatively-free position in the amphiphilic block polymer molecule. At this time, two or more marker groups may be bound to one molecule of the amphiphilic block polymer.

The following (6) to (13) relate to a molecular assembly.

The term "molecular assembly" refers to a structure formed by aggregation or self-assembling orientation and association of molecules of the amphiphilic block polymer described above.

(6) A molecular assembly comprising one or more kinds of molecules of the amphiphilic block polymer according to any one of the above (1) to (5).

(7) The molecular assembly according to the above (6), which has a particulate form.

The molecular assembly according to the above (7) may be used as a carrier for drug delivery system or molecular imaging system.

(8) The molecular assembly according to the above (7), which is a hollow particle.

As described in the following (9) to (11), the hollow particle according to the above (8), that is, a vesicle can hold a substance therein. In this specification, such type of molecular assembly is also referred to as an "encapsulated type" molecular assembly. The molecular assembly according to the following (9) to (11) may be used as an encapsulated type carrier.

(9) The molecular assembly according to the above (8), which is a particle having an aqueous phase therein.

(10) The molecular assembly according to the above (9), wherein the aqueous phase contains a drug.

(11) The molecular assembly according to the above (9) or (10), wherein the aqueous phase contains a signal agent and/or a ligand.

In the above (11), the term "signal agent" refers to a substance that can be detected for imaging, and includes fluorescent agents, radioactive element-containing substances, magnetic substances, and the like.

In the above (11), the term "ligand" includes one which can coordinate to a molecule or an atom of a drug or a signal agent to be delivered to a target region when the molecular assemblies are administered.

Further, in this specification, the molecular assembly comprising the amphiphilic block polymer having a marker group bound thereto, such as the amphiphilic block polymer according to the above(3), is also referred to as a "binding type" molecular assembly. The present invention includes a binding type molecular assembly, an encapsulated type molecular assembly, and a molecular assembly having characteristics of both types.

In a case where the molecular assembly is composed of the amphiphilic block polymer having a marker group bound to a terminal structural unit of the molecule thereof, such as the amphiphilic block polymer according to the above (4), as described in the following (12), such a binding type molecular assembly has a surface modified by the marker group.

(12) The molecular assembly according to any one of the above (6) to (11), wherein when a marker group is present, the marker group is exposed at the surface of the molecular assembly.

In a case where the molecular assembly is composed of the amphiphilic block polymer having a marker group bound to a structural unit of the molecule thereof, such as the amphiphilic block polymer according to the above (5), such a binding type molecular assembly has a membrane tissue having the marker group held therein by, for example, embedding.

(13) The molecular assembly according to any one of the above (6) to (12), which has a particle size of 10 to 500 nm.

In the above (13), the term "particle size" refers to a particle size observed with highest frequency in a particle size distribution, that is, a median particle size.

The following (14) and (15) relate to a molecular probe using the molecular assembly described above and a drug delivery system (DDS) using the molecular probe.

(14) A molecular probe for drug delivery system, comprising the molecular assembly according to any one of the above (10) to (13).

(15) A drug delivery system comprising administration of the molecular assembly according to any one of the above (10) to (13) into a living body.

The molecular assembly used in the above (14) and (15) can be of at least one type selected from a type having a drug-containing aqueous phase therein and a type having a drug coordinated by a ligand.

The following (16) and (17) relate to a molecular probe using the molecular assembly described above and a molecular imaging system using the molecular probe.

(16) A molecular probe for molecular imaging system, comprising the molecular assembly according to any one of the above (11) to (13).

(17) A molecular imaging system comprising administration of the molecular assembly according to any one of the above (11) to (13) into a living body.

The molecular assembly used in the above (16) and (17) can be of at least one type selected from a type having a signal agent-containing aqueous phase therein, a type having a signal group introduced thereinto via a covalent bond, and a type having a signal agent coordinated by a ligand.

According to the present invention, it is possible to provide a novel amphiphilic substance. By forming a molecular assembly using the amphiphilic substance, it is possible to provide a nanoparticle which has high biocompatibility, stability, and biodegradability as a nanocarrier. Further, by introducing various substituent groups into the amphiphilic substance, it is possible to easily form variously modified nanoparticles.

By allowing the nanoparticle according to the present invention to be prepared so as to contain a drug, it is possible to provide a probe useful for drug delivery system. This probe enables the drug to specifically accumulate in a diseased or affected part so that the drug can act on the cells of the diseased or affected part.

Further, by allowing the nanoparticle according to the present invention to be prepared so as to contain a signal agent, it is possible to provide a probe useful for molecular imaging system. This probe enables the signal agent to specifically accumulate in a diseased or affected part so that the diseased or affected part can be imaged.

The nanoparticle according to the present invention is at least equal in retention in the blood to a nanoparticle modified by a water-soluble polymeric compound, polyethylene glycol (PEG), which is conventionally known as a nanoparticle having excellent properties.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

[1. Amphiphilic Block Polymer]

Figure 1:
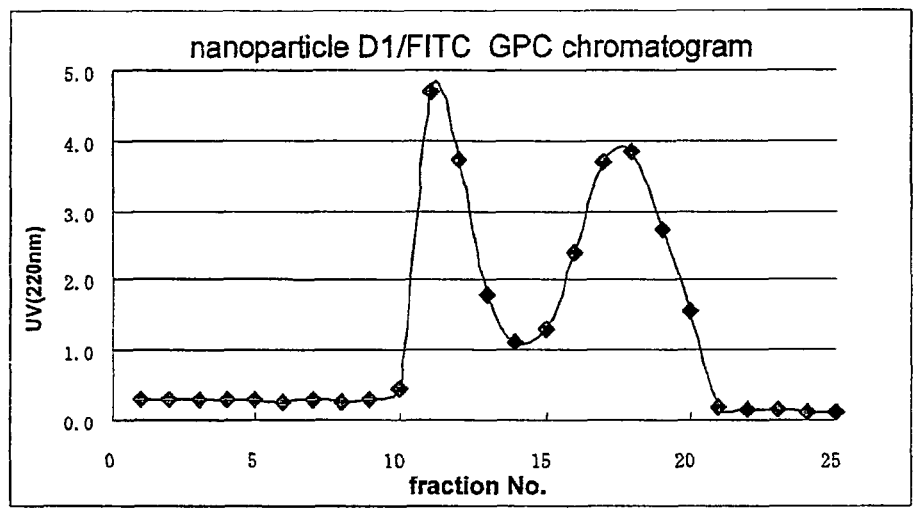
FIG. 1 is a GPC chromatogram of fluorescent agent-encapsulated nanoparticles D1/FITC prepared in Example 8.

An amphiphilic block polymer according to the present invention comprises the following hydrophilic block and hydrophobic block. In the present invention, the term "amino acid" refers to natural amino acids, unnatural amino acids, and derivatives thereof obtained by modification and/or chemical alteration, and includes α-, β-, and γ-amino acids. Preferably, α-amino acids are used.

[1-1. Hydrophilic Block]

The hydrophilic block is a hydrophilic polypeptide chain having 10 or more structural units derived from sarcosine. Sarcosine is highly water-soluble, and a polymer thereof is highly flexible because it is an N-substituted amide and therefore can be more easily cis-trans isomerized as compared to a normal amide group and steric hindrance around the Cα carbon atom is low. The use of such a polypeptide having both high hydrophilicity and high flexibility is important to the present invention. That is, any polypeptide having such basic characteristics can be used in the present invention.

The upper limit of the number of the sarcosine units is not particularly limited, but is about 500. In the present invention, a polypeptide chain having about 10 to 200, preferably about 10 to 100 units is often synthesized. If the number of the units exceeds about 500, synthesis of a polypeptide chain is difficult per se. If the number of the units exceeds about 200, when a molecular assembly is formed, the resulting molecular assembly tends to lack stability. If the number of the sarcosine units is less than about 10, formation of a molecular assembly is difficult per se.

[1-2. Hydrophobic Block]

The hydrophobic block is a hydrophobic molecular chain comprising units selected from the group consisting of amino acid-derived structural units and hydroxyl acid-derived structural units as essential structural units, and having 5 or more of the essential structural units. Specific examples of the hydrophobic molecular chain include a hydrophobic polypeptide chain having 5 or more hydrophobic amino acid units, a hydrophobic polyester chain having 5 or more hydroxyl acid units, and a hydrophobic depsipeptide chain having a total of 5 or more of both amino acid and hydroxyl acid units.

In the present invention, the degree of "hydrophobicity" of the hydrophobic block is not particularly limited, but at least, the hydrophobic block shall be hydrophobic enough to be a region relatively more hydrophobic than the hydrophilic block having 10 or more sarcosine units so that the molecule of a copolymer composed of the hydrophobic block and the hydrophilic block can have amphiphilicity as a whole or so that the amphiphilic block polymer can self-assemble in a solvent to form a self-assembly, preferably a particulate self-assembly.

Many of hydrophobic amino acids have an aliphatic side chain, an aromatic side chain, and the like. Examples of natural amino acids include glycin, alanine, valine, leucine, isoleucine, proline, methionine, tyrosine, and tryptophan. Examples of unnatural amino acids include, but are not limited to, amino acid derivatives such as γ-methyl glutamate, γ-benzyl glutamate, β-methyl aspartate, β-ethyl aspartate, and β-benzyl aspartate. Examples of hydroxyl acids include, but are not limited to, glycolic acid, lactic acid, and hydroxyisobutyric acid.

The kinds of structural units constituting the hydrophobic molecular chain and their ratio may be appropriately set by those skilled in the art so that the molecular chain can be hydrophobic as a whole.

The upper limit of the number of structural units of the hydrophobic molecular chain is not particularly limited, but is about 500. In the present invention, a hydrophobic molecular chain having about 5 to 200, preferably about 10 to 100 structural units is often synthesized. If the number of the structural units exceeds about 500, synthesis of a hydrophobic molecular chain is difficult per se. If the number of the structural units exceeds about 200, when a molecular assembly is formed, the resulting molecular assembly tends to lack stability. If the number of the structural units is less than 5, formation of a molecular assembly is difficult per se.

[1-3. Marker Group etc.]

The amphiphilic block polymer molecule may further comprise a group appropriately selected by those skilled in the art. Examples of such a group include organic groups having an appropriate chain length and functional groups. For example, in a case where the amphiphilic block polymer forms into a molecule assembly as a carrier for drug delivery system or molecular imaging system (which will be described in the following "2. Molecular Assembly"), such a group makes it possible to allow the molecular assembly of the amphiphilic block polymer to have form and function so that the molecular assembly can be useful as such a carrier. Examples of the functional groups include marker groups including a signal group and a ligand (which will be described later), polysaccharides such as carboxymethylcellulose and amylose, and water-soluble polymers such as polyalkylene oxide chains, polyethylene glycol chains, and polyvinyl alcohol chains.

[1-3-1. Signal Group]

A signal group is a group that can be detected for imaging. Examples of such a signal group include fluorescent groups, radioactive element-containing groups, and magnetic groups. Means for detecting these groups may be appropriately selected by those skilled in the art.

Examples of the fluorescent groups include, but are not limited to, groups derived from fluorescein-based pigments, cyanine-based pigments such as indocyanine pigments, rhodamine-based pigments, and quantum dots. In the present invention, near-infrared fluorescent groups (e.g., groups derived from cyanine-based pigments or quantum dots) are particularly preferably used.

Examples of the radioactive element-containing groups include, but are not limited to, groups derived from saccharides, amino acids, or nucleic acids labeled with a radioisotope such as $^{18}$F.

Examples of the magnetic groups include, but are not limited to, groups having a magnetic substance such as ferrichrome and groups contained in ferrite nanoparticles or magnetic nanoparticles.

[1-3-2. Ligand]

Examples of a ligand include one for allowing a molecular assembly of the amphiphilic block polymer according to the present invention to specifically bind to a target region when the molecular assemblies are administered, and one which can coordinate to a molecule or an atom of a drug or a signal agent to be delivered to a target region when the molecular assemblies are administered.

As a ligand for targeting to allow a molecular assembly to specifically bind to a target region, a conventional ligand known to those skilled in the art may be used without any limitation, and examples thereof include antibodies and adhesion factors such as RGD (arginine-glycin-aspartic acid).

As a ligand for coordinating to a molecule or an atom of a drug or a signal agent to be delivered to a target region, a conventional ligand known to those skilled in the art can be used without any limitation, and an example thereof includes tricarboxylic acid which can coordinate to a transition metal.

[1-3-3. Binding Type of Marker Group]

One or more marker groups may be bound to one molecule of the amphiphilic block polymer. The term "bound" specifically refers to covalent bonding and includes direct bonding to a specific part of the polymer and indirect bonding to a specific part of the polymer through an appropriate spacer group. The spacer group is not particularly limited and may be appropriately selected by those skilled in the art, and examples thereof include alkyl groups, polysaccharides such as carboxymethylcellulose and amylose, and water-soluble polymers such as polyalkylene oxide chains, polyethylene glycol chains, and polyvinyl alcohol chains.

For example, the marker group may be bound to an end of the amphiphilic block polymer directly or indirectly. This binding type is preferably used in a case where the marker group is relatively bulky (e.g., groups derived from polymers, such as peptides, or fluorescent substances) or in a case where a molecular assembly of the amphiphilic block polymer is made to have a surface modified by the marker group. In the case of this binding type, one marker group is often introduced into one molecule of the amphiphilic block polymer.

Further, for example, the marker group may be bound to the structural unit of the amphiphilic block polymer directly or indirectly. In this case, the structural group unit to which the marker group is to be bound includes at least an inner structural unit of both inner and terminal structural units of the amphiphilic block polymer molecule. Therefore, the marker group may be bound to a relatively-free position in the amphiphilic block polymer molecule. This binding type is preferably used in a case where the marker group is relatively small in volume (e.g., radioactive element-containing groups) or in a case where a molecular assembly of the amphiphilic block polymer is made to have a membrane tissue having the marker group held therein by, for example, embedding. In the case of this binding type, two or more marker groups are often introduced into one molecule of the amphiphilic block polymer.

[1-4. Synthesis Method of Amphiphilic Block Polymer]

A method for synthesizing the amphiphilic block polymer according to the present invention is not particularly limited, and any conventional peptide synthesis method, polyester synthesis method, and/or depsipeptide synthesis method may be used.

Peptide synthesis may be carried out by, for example, ring-opening polymerization of N-carboxyamino acid anhydride (amino acid NCA) using a base, such as amines, as an initiator.

Polyester synthesis may be carried out by, for example, ring-opening polymerization of lactide using a base, such as amines, as an initiator.

Depsipeptide synthesis may be carried out by the following method.

For example, a benzyl ester derivative is derived from a hydroxy acid, and an N-protected amino acid is extended according to a peptide synthesis method. Then, the benzyl ester is removed and replaced with an active ester to give an N-protected oligodepsipeptide active ester, and then an N-protecting group is removed therefrom to polycondense an oligodepsipeptide active ester having a free amino group.

Alternatively, for example, a free hydroxy acid may be reacted with nitrophenylsulphenyl (Nps)-amino acid N-carboxylic acid anhydride in the presence of pyridine to synthesize N-Nps-didepsipeptide.

[1-5. Others]

The molecular weight of the amphiphilic block polymer according to the present invention is not particularly limited. For example, in a case where the amphiphilic block polymer forms into a molecule assembly as a carrier for drug delivery system or molecular imaging system (which will be described in the following "2. Molecular Assembly"), the molecular weight of the amphiphilic block polymer is appropriately determined by those skilled in the art in view of the kind of substance to be held by the carrier, the effective concentration of the substance, and the duration of release of the substance.

[2. Molecular Assembly]

A molecular assembly according to the present invention is a structure formed by aggregation or self-assembling orientation and association of molecules of the amphiphilic block polymer according to the present invention. Therefore, the form of the molecular assembly according to the present invention is not particularly limited, and examples thereof include vesicle, micelle, rod, and other various forms obtained by molecular aggregation. By controlling the molecular structure or interaction point of the amphiphilic block polymer, it is possible to form molecular assemblies having various forms.

In a case where the molecular assembly according to the present invention has a particulate form, such as vesicle or micelle, the molecular assembly may be used as a carrier for drug delivery system or molecular imaging system.

The molecular assembly according to the present invention is preferably a vesicle which is a hollow particle. Usually, a vesicle has a lumen which provides an aqueous phase. Therefore, it is possible to allow the aqueous phase to contain a substance to be encapsulated in the molecular assembly. In the present invention, this type of molecular assembly is referred to as an "encapsulated type molecular assembly".

On the other hand, in a case where the molecular assembly according to the present invention is formed with comprising the amphiphilic block polymer having a marker group bound thereto, this type of molecular assembly is referred to as a "binding type molecular assembly". The present invention includes a binding type molecular assembly, an encapsulated type molecular assembly, and a molecular assembly having characteristics of both types.

[2-1. Encapsulated Type Molecular Assembly]

Examples of the substance to be encapsulated in the encapsulated type molecular assembly include drugs, signal substances, and ligands. Such a substance may be encapsulated in the molecular assembly in the form of a solution or a suspension liquid isotonic with external environment of the molecular assembly.

The drug to be encapsulated in the molecular assembly is not particularly limited as long as it is suited to a target disease, and specific examples thereof include anticancer drugs, antibacterial agents, antiviral drugs, anti-inflammatory agents, immune-suppressing drugs, steroid drugs, hormone drugs, and antiangiogenic agents.

These drugs may be used singly or in combination of two or more of them.

The signal agent is a substance that can be detected for imaging, and examples thereof include fluorescent agents, radioactive element-containing substances, and magnetic agents.

Examples of the fluorescent agents include, but are not limited to, fluorescein-based pigments, cyanine-based pigments such as indocyanine, rhodamine-based pigments, and quantum dots. In the present invention, near-infrared fluorescent agents (e.g., cyanine-based pigments, quantum dots) are particularly preferably used.

Examples of the radioactive element-containing substances include, but are not limited to, saccharides, amino acids, or nucleic acids labeled with a radioisotope such as $^{18}F$.

Examples of the magnetic agents include, but are not limited to, magnetic substances, such as ferrichrome, ferrite nanoparticles, and magnetic nanoparticles.

The ligand includes one for coordinating to a molecule or an atom of a drug or a signal agent to be delivered to a target region when the molecular assemblies are administered. As such a ligand, a conventional one known to those skilled in the art may be used without any limitation, and an example thereof includes tricarboxylic acid which can coordinate to a transition metal.

The signal agents and the ligands may be used singly or in combination of two or more of them.

[2-2. Binding Type Molecular Assembly]

In a case where the molecular assembly is composed of the amphiphilic block polymer having a marker group bound to a terminal structural unit of the molecule thereof, such a binding type molecular assembly may have a surface modified by the marker group. That is, the marker group may be exposed at the surface of the molecular assembly.

On the other hand, in a case where the molecular assembly is composed of the amphiphilic block polymer having a marker group bound to at least an inner structural unit of the structural units of the amphiphilic block polymer molecule, such a binding type molecular assembly may have a membrane tissue having the marker group held therein by, for example, embedding.

In the case of the binding type molecular assembly, two or more marker groups may be contained in one molecular assembly. For example, the molecular assembly may be formed using two or more kinds of the amphiphilic block polymers having one marker per molecule, or using one kind of the amphiphilic block polymer having two or more markers per molecule. Of course, the molecular assembly may be formed using two or more kinds of the amphiphilic block polymers having two or more markers per molecule.

[2-3. Method for Forming Molecular Assembly]

A method for forming the molecular assembly is not particularly limited and may be appropriately selected by those skilled in the art according to desired shape, size, and properties of a molecular assembly to be formed and the kind, properties, and amount of a substance to be held by the molecular assembly. Examples of a method for forming the molecular assembly include an injection method, an ultrasonic method, and an extrusion method.

Among these methods, an injection method is often used in the present invention. According to an injection method, a molecular assembly may be formed by dissolving the amphiphilic block polymer in an organic solvent such as trifluoroethanol, ethanol, hexafluoroisopropanol, or dimethylsulfoxide to obtain a solution, dispersing the solution in a water-based solvent such as distilled water for injection, normal saline, or buffer, subjecting the dispersion liquid to treatment for purification such as gel filtration chromatography, filtering, or ultracentrifugation, and removing the organic solvent.

In a case where the molecular assembly is formed as a vesicle, particularly as an encapsulated type, it is preferred that in a water-based solvent such as distilled water for injection, normal saline, or buffer, a substance to be encapsulated in the molecular assembly is dissolved or suspended to obtain an aqueous solution or a suspension liquid, in the obtained aqueous solution or suspension liquid, a solution which is prepared by the amphiphilic block polymer is dissolved in the above-described organic solvent is dispersed.

Further, the molecular assembly formed using the amphiphilic block polymer according to the present invention may further be subjected to surface modification according to a well-known method.

[2-4. Others]

The particle size of the molecular assembly having a particulate form is in the range of about 10 to 500 nm. A particulate molecular assembly having a particle size less than 10 nm is difficult to form, while a particulate molecular assembly having a particle size larger than 500 nm is not suitable, especially when administered into a living body by injection.

The size of the molecular assembly can be controlled by changing the chain length of the amphiphilic block polymer according to the present invention.

[3. Molecular Probe and Drug Delivery System and Molecular Imaging System Using the Molecular Probe]

The molecular assembly according to the present invention is suitable for drug delivery system and molecular imaging system. Hereinafter, the molecular assembly intended to be used for such system will also be referred to as a "nanoparticle".

In a case where the nanoparticle according to the present invention contains a drug, the nanoparticle is suitable as a molecular probe for drug delivery system. Such a drug-containing nanoparticle may be of a type selected from one having a drug-containing aqueous phase therein and one containing a drug coordinated by a ligand.

Further, in a case where the nanoparticle according to the present invention contains a signal agent (or signal group), the nanoparticle is suitable as a molecular probe for molecular imaging system. Such a signal agent (or signal group)-containing nanoparticle may be of a type selected from one having a signal agent-containing aqueous phase therein, one having a signal group introduced thereinto via a covalent bond, and one containing a signal agent coordinated by a ligand. Specific examples of a molecular probe for molecular imaging system include a PET probe and an MRI probe.

Furthermore, in the case where the nanoparticle according to the present invention contains both of a drug and a signal agent (or signal group), the nanoparticle is suitable as a molecular probe for both drug delivery system and molecular imaging system.

The nanoparticle according to the present invention is stable in the blood and has excellent biocompatibility. Further, by introducing various groups into the amphiphilic block polymer to form a nanoparticle, it is possible to allow the molecular assembly to have various functions.

For example, by introducing a group having an affinity for a living body into the amphiphilic block polymer, it is possible to allow a nanoparticle to selectively bind to a specific living tissue. Therefore, by encapsulating, for example, a magnetic substance, a radioactive substance, or a fluorescent substance (particularly, a near-infrared fluorochrome enabling noninvasive molecular imaging) into the nanoparticles, it is possible to allow the nanoparticles to specifically accumulate in a diseased or affected part, thereby enabling diagnosis using various diagnostic apparatuses.

Further, the amphiphilic block polymer constituting the nanoparticle according to the present invention is not stored in a living body because it is mainly composed of a peptide block and, if necessary, a block of a biodegradable polymer other than peptide, and is therefore quickly degraded by a protein metabolism system in a living body after administration.

Further, the size, shape, tissue selectivity, and degradation speed in a living body of the particle and the sustainability of a drug or a signal agent encapsulated in the particle can be controlled by changing the chain length of the amphiphilic peptide. Further, the properties of the particle can be controlled also by using the amphiphilic peptides different in composition and molecular weight in combination.

EXAMPLES

Hereinbelow, the present invention will be described in more detail with reference to the following examples, but the present invention is not limited to these examples. It is to be noted that in the following examples, "N,N-dimethylformamide" refers to one subjected to simple distillation twice, unless otherwise specified.

Example 1

Synthesis of Compound (a) (Example Obtained by Introducing Hydrophobic Block into N Terminal of Sar Chain)

1.0 mL of an N,N-dimethylformamide solution containing 5.7 µL of n-hexylamine was added to 4.4 mL of an N,N-dimethylformamide (DMF) solution containing 100 mg of sarcosine-NCA (Sar-NCA) (NCA: amino acid N-carboxy anhydride) in an argon gas atmosphere. The thus obtained solution was stirred at room temperature for about 5 hours under reduced pressure. To the solution, 8.6 mL of an N,N-dimethylformamide solution containing 150 mg of alanine-NCA (Ala-NCA) was added, and the resulting solution was stirred overnight at room temperature under reduced pressure. Then, diethyl ether was added to the solution to obtain precipitation. The precipitation was washed several times with diethyl ether, and was then dried under reduced pressure to obtain 60 mg of a white solid compound (a).

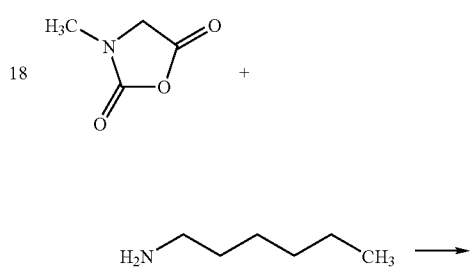

Scheme 1

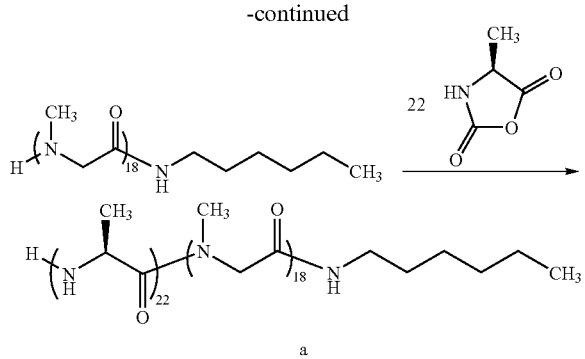

The compound (a) was identified by ¹H-NMR (400 MHz, TFA-d). As a result, the peak of N-methyl group of sarcosine was observed at 3.21 ppm and the peak of terminal methyl group was observed at 0.86 ppm. The integral ratio between these two peaks (N-methyl group:terminal methyl group) was 54:3.

Example 2

Synthesis of Compound (b) (Example Obtained by Introducing Functional Group into C Terminal)

1.0 mL of an N,N-dimethylformaide solution containing 14 mg of 5-amino-2-(bis((methoxycarbonyl)methyl)amino) methyl hexanoate was added to 4.4 mL of an N,N-dimethylformamide solution containing 100 mg of sarcosine-NCA (Sar-NCA) in an argon gas atmosphere. The thus obtained solution was stirred at 50° C. for about 5 hours under reduced pressure. To the solution, 8.6 mL of an N,N-dimethylformamide solution containing 150 mg of alanine-NCA (Ala-NCA) was added, and the resulting solution was stirred overnight at 50° C. under reduced pressure. Then, diethyl ether was added to the solution to obtain precipitation. The precipitation was washed several times with diethyl ether, and was then dried under reduced pressure to obtain 50 mg of a white solid compound (b0).

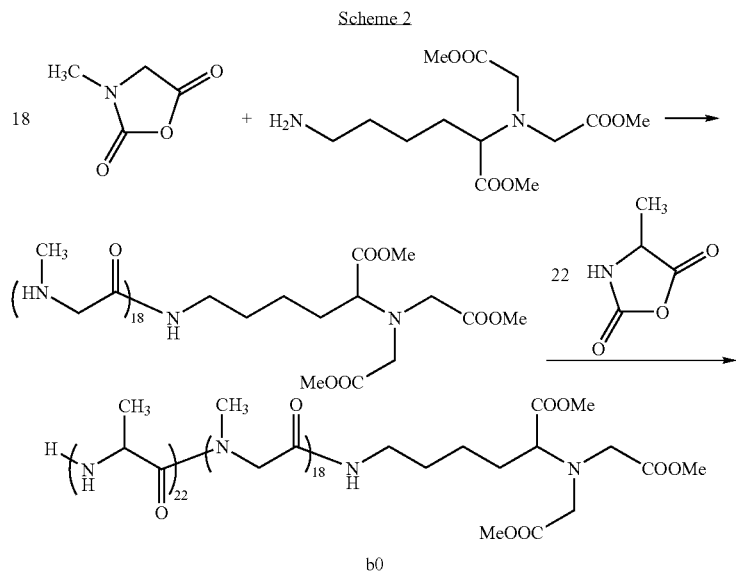

10 equivalents of a 1.0 mol/L aqueous sodium hydroxide solution was added to 20 mL of a methanol solution containing 50 mg of the compound (b0) and stirred for 4 hours. To the solution, 1.0 mol/L hydrochloric acid was added to terminate reaction, and the solution was dried under reduced pressure and dissolved in methanol. The thus obtained methanol solution was centrifuged to collect supernatant, and then the supernatant was dried under reduced pressure to obtain 40 mg of a white solid compound (b).

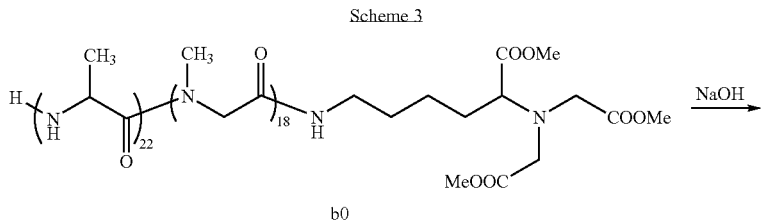

-continued

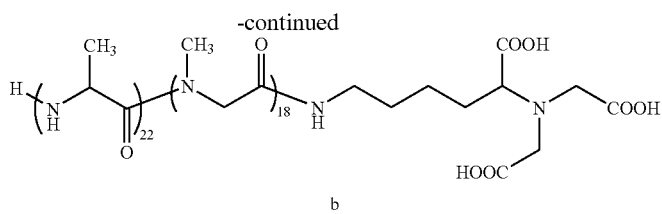

b

Example 3

Synthesis of Compound (c) (Example Obtained by Introducing Hydrophobic Polyester Chain into N Terminal)

0.05 eq. of 2-methoxyethylamine dissolved in nitrobenzene was added to a nitrobenzene solution of sarcosine-NCA (Sar-NCA) (200 mg, 1.0 eq.) so that the concentration of Sar-NCA was 0.3 M. The thus obtained solution was stirred at room temperature for 3 hours in an argon gas atmosphere. Then, 0.3 eq. of lactide dissolved in a small amount of nitrobenzene was added to the solution and further stirred at 120° C. overnight. The reaction solution was subjected to distillation under reduced pressure to remove the solvent therefrom, and was then purified by size exclusion chromatography LH20 (eluant:DMF) and reprecipitated in diethyl ether to collect a compound (c).

Scheme 4

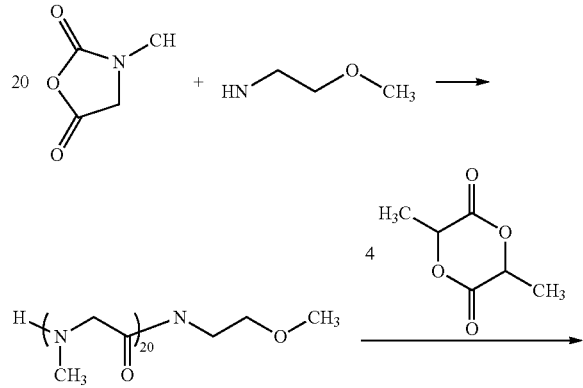

-continued

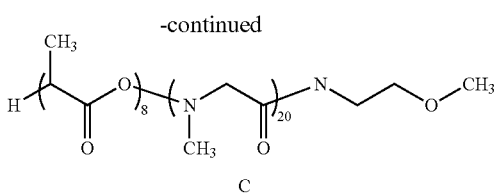

c

Example 4

Synthesis of Compound (d1) (Example Obtained by Introducing Hydrophobic Peptide Block into C Terminal of Sar Chain)

2.93 mg of n-hexylamine dissolved in 1.0 mL of N,N-dimethylformamide was added to an N,N-dimethylformamide solution (4.0 mL) containing 108 mg of glutamic acid methyl ester-NCA (Glu(OMe)-NCA) in an argon gas atmosphere.

The reaction solution was stirred at room temperature for 3 hours in an argon gas atmosphere. Then, an N,N-dimethylformamide solution (4 mL) containing 200 mg of sarcosine-NCA (Sar-NCA) was added to the reaction solution and stirred overnight at room temperature in an argon gas atmosphere. Thereafter, the reaction solution was cooled in an ice bath, and then glycolic acid (5.0 eq.), o-(benzotriazole-1-yl)-N,N,N',N'-tetramethyluronium hexafluorophosphate (HATU) (5.0 eq.), and N,N-diisopropylethylamine (DIEA) (7.5 eq.) were added to the reaction solution and stirred at 0° C. for 1 hour and further stirred at room temperature for 10 hours. Then, HATU (2.5 eq.) and DIEA (3.0 eq.) were further added to the reaction solution, stirred at room temperature for 10 hours, and then subjected to distillation under reduced pressure to remove the solvent therefrom. The thus obtained crude product was purified using an LH20 column (eluant: DMF), and was then reprecipitated in DMF/diethyl ether to collect precipitation. The precipitation was dried under vacuum.

Scheme 5

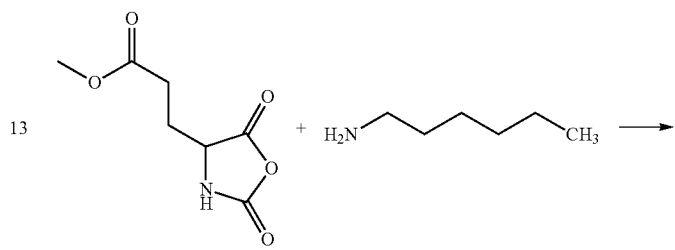

-continued

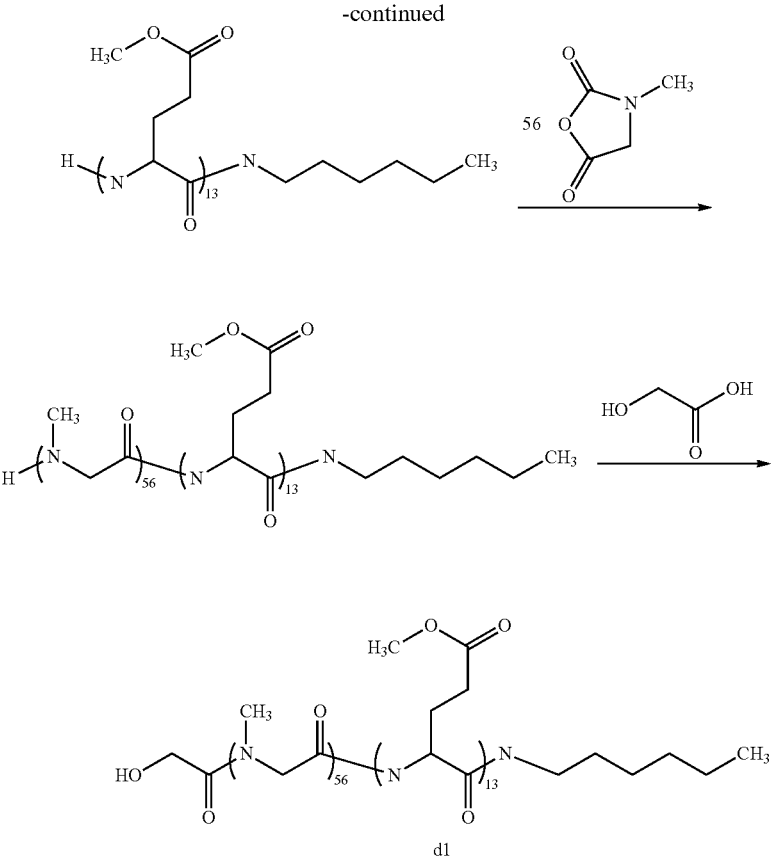

It has been found that by partially or entirely replacing molecules of the glutamic acid methyl ester-NCA used in Example 4 with molecules of glutamic acid methyl ester-NCA containing a stable isotope as a constituent element thereof, it is clearly possible to introduce one or more stable isotope labels. This finding indicates that by introducing a stable isotope into a chain structural unit, it is possible to easily synthesize a PET probe or the like.

Example 5

Synthesis of Compound (d2) (Example Obtained by Introducing Hydrophobic Peptide Block into C Terminal of Sar Chain)

2.93 mg of n-hexylamine dissolved in 1.0 mL of N,N-dimethylformamide was added to an N, N-dimethylformamide solution (4.0 mL) containing 108 mg of glutamic acid methyl ester-NCA (Glu(OMe)-NCA) in an argon gas atmosphere.

The reaction solution was stirred at room temperature for 3 hours in an argon gas atmosphere. Then, an N,N-dimethylformamide solution (4 mL) containing 133 mg of sarcosine-NCA (Sar-NCA) was added to the reaction solution and stirred overnight at room temperature in an argon gas atmosphere. Thereafter, the reaction solution was cooled in an ice bath, and then glycolic acid (5.0 eq.), HATU (5.0 eq.), and DIEA (7.5 eq.) were added to the reaction solution, stirred at 0° C. for 1 hour, and further stirred at room temperature for 10 hours. Then, HATU (2.5 eq.) and DIEA (3.0 eq.) were further added to the reaction solution, stirred at room temperature for 10 hours, and was then subjected to distillation under reduced pressure to remove the solvent therefrom. The thus obtained crude product was purified using an LH20 column (eluant: DMF), and was then reprecipitated in DMF/diethyl ether to collect precipitation. The precipitation was dried under vacuum.

Scheme 6

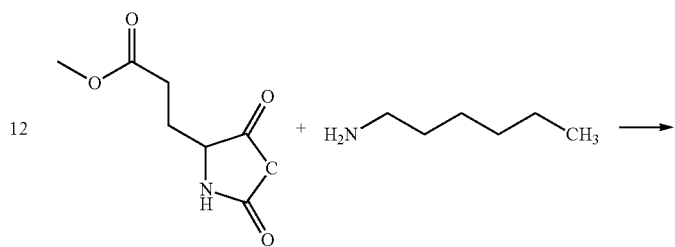

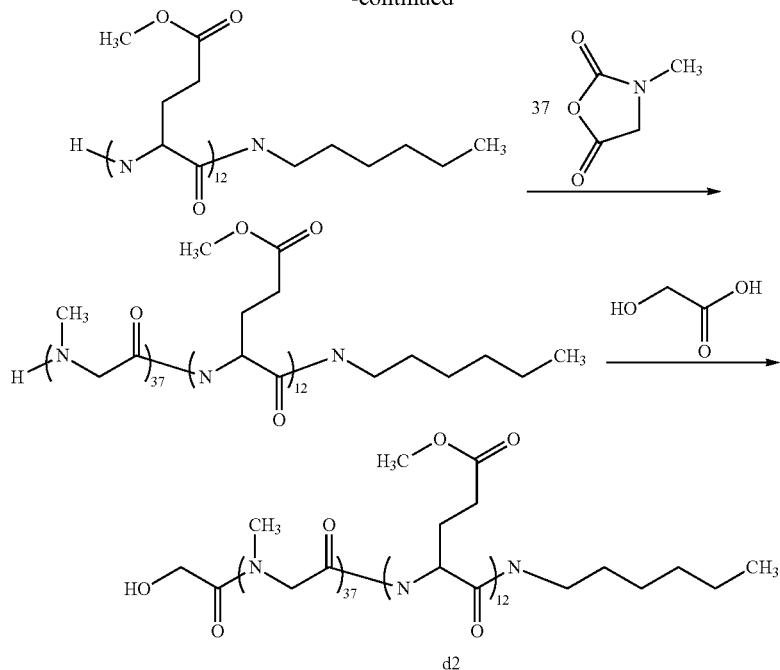

Example 6

Synthesis of Compound d1-ICG (Example Obtained by Introducing Fluorochrome)

1 mg of ICG-sulfo-OSu (1 µmol, 1.3 eq.) dissolved in a DMF solution (0.1 mL) was added to a DMF solution (0.2 mL) containing 5 mg (0.9 µmol, 1.0 eq.) of the peptide d1, and the resulting solution was stirred at room temperature for about 7 hours. Then, 0.4 mg of HATU (1 µmol, 1.5 eq.) and 0.26 µL of DIEA (1.5 µmol, 2.25 eq.) were further added to the solution in an ice bath, and stirred. After a lapse of 1 hour, the solution was returned to room temperature and was further stirred overnight. Thereafter, 0.23 mg of glycolic acid (3.3 µmol, 5.0 eq.), 1.3 mg of HATU (3.3 µmol, 5.0 eq.), and 0.88 µL of DIEA (5.0 µmol, 7.5 eq.) were added to the solution, stirred overnight, and subjected to distillation under reduced pressure to remove the solvent therefrom. As a result, it was possible that the fluorescent agent (ICG-sulfo-OSu) was introduced into the amphiphilic peptide via an amide bond. The thus obtained crude product Kas purified using an LH20 column (eluant:DMF) (5.7 mg, 0.88 µmol).

Scheme 7

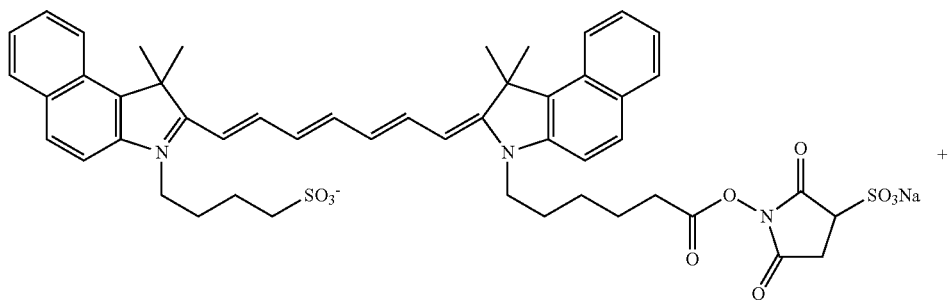

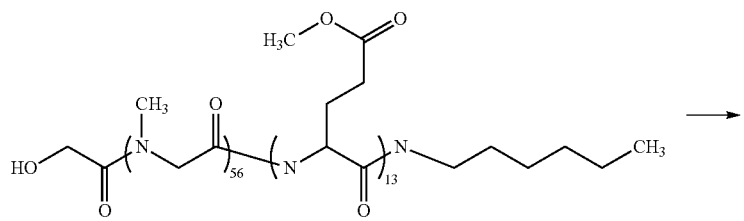

-continued

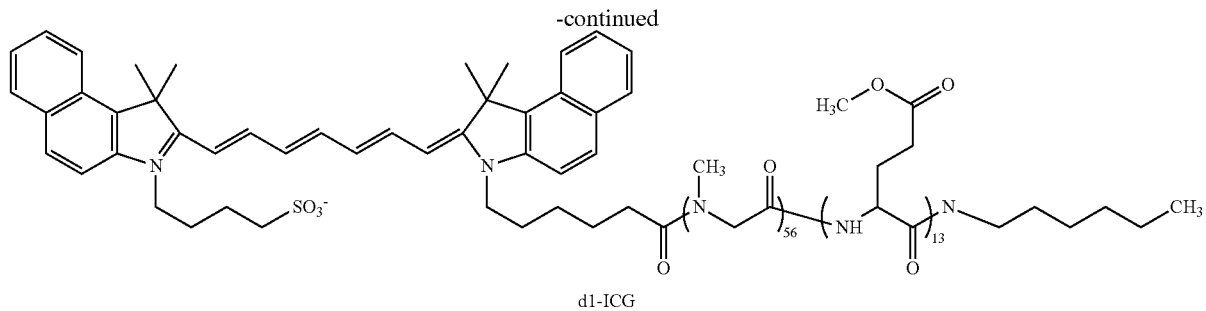

d1-ICG

In each of the Examples 1 to 6, am amphiphilic block polymer having a structure represented by the above chemical formula was synthesized, but by changing the kind of initiator and the ratio of monomers, it is possible to synthesize a hydrophilic block and a hydrophobic block having their respective desired lengths.

Example 7

Formation of Nanoparticles

Nanoparticles were formed using the compounds (a), (b), (c), (d1), and (d2) synthesized in the above Examples 1 to 6.

Each of the compounds (b), (c), (d1), and (d2) was dissolved singly in 2,2,2-trifluoroethanol, and the resulting solution was dispersed in water or buffer in an atmosphere having a temperature of 0° C. to obtain a nanoparticle dispersion liquid. The compounds (a) and (b) were dissolved in 2,2,2,-trifluoroethanol in a molar ratio of a:b=1:99, 5:95, or 20:80 to obtain a solution. The solution was dispersed in water or buffer in an atmosphere having a temperature of 0° C. to obtain a nanoparticle dispersion liquid. The 2,2,2-trifluoroethanol contained in the nanoparticle dispersion liquid was removed by gel filtration chromatography (support: Sephacryl™ S-100 HR (Amersham biosciences), eluant: 20 mM phosphate buffer (pH 7.4) in which 0.5 M NaCl had been dissolved).

The nanoparticle dispersion liquid was filtered through a 0.8 μm filter, and was then subjected to dynamic light scattering analysis to measure an average particle size. The measurement results are shown in Table 1. As shown in Table 1, nanoparticles having a diameter of several tens of nm to several hundred nm were formed.

TABLE 1

| nanoparticle | compound (mixing ratio) | particle size (nm) |
| --- | --- | --- |
| B | b | 35 |
| AB | a, b (a:b = 1:99) | 40 |
|  | a, b (a:b = 5:95) | 40 |
|  | a, b (a:b = 20:80) | 50 |
| C | c | 50 |
| D1 | d1 | 100 |
| D2 | d2 | 240 |

The result of above Example 7 teaches as follows. Though the amphiphilic compounds (a) and (b) are different in whether they have a functional group or not, from the results about the nanoparticles (B) and (AB), it has been found that the difference in functional group does not have great influence on the particle size of the resulting nanoparticles. From another standpoint, it has also been found that the particle size of the nanoparticles can be finely controlled by changing the mixing ratio of the amphiphilic compounds.

On the other hand, from the results about the nanoparticles (C), (D1), and (D2), it has been found that the difference in the chain length of the amphiphilic compound has a relatively great influence on the particle size of the resulting nanoparticles. That is, it has been found that the size of the nanoparticles can be easily changed by changing the chain length of the amphiphilic compound.

Example 8

Formation of Fluorescent Agent-Encapsulated Nanoparticles D1/FITC

In this example, a fluorescent agent FITC was encapsulated into vesicles (nanocapsules) D1 formed of the compound d1 to obtain fluorescent agent-encapsulated nanoparticles D1/FITC.

4 mg of the compound d1 was dissolved in 72 μL of 2,2,2-trifluoroethanol (TFE) to obtain a solution, and the solution was injected into 1.5 mL of 10 mM Tris-HCl buffer (pH 7.4) containing 5 mg of FITC-dextran (molecular weight: 4,000) in an atmosphere having a temperature of 0° C. to form nanoparticles, followed by stirring in an ice bath for 10 minutes, and gel filtration chromatography for purification.

Figure 2:
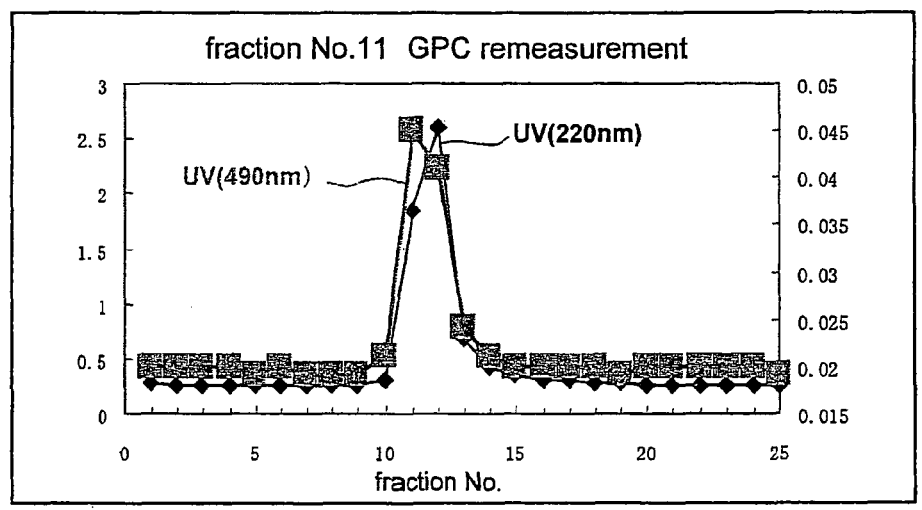
FIG. 2 is a GPC chromatogram of fraction No. 11 shown in FIG. 1 using the same column and the same conditions as FIG. 1.

The nanoparticles were analyzed by gel permeation chromatography (GPC). FIG. 1 shows a GPC chromatogram. Fraction No. 11 shown in FIG. 1 was fractionated and then again subjected to gel permeation chromatography using the same column under the same conditions. The thus obtained GPC chromatogram is shown in FIG. 2. Separation conditions are shown below.

Analysis Conditions of D1/FITC by GPC
  Column Support: Sephacryl S-100 (GE health care)
  Eluant: 10 mM Tris-HCl pH 7.4 buffer solution
  Amount of Each Fraction: 40 drops/tube
  Temperature: 4° C.
  Detection Wavelength: 220 nm and 490 nm As shown in FIG. 1, a peak derived from the nanocapsule D1 part of D1/FITC formed as a particle was observed around fraction No. 11, and a peak derived from a molecular assembly not formed as a particle was observed in fractions No. 20 or more. Further, as shown in FIG. 2, a peak derived from the nanocapsule D1 part of the nanoparticles D1/FITC and a peak derived from the fluorescent agent FITC encapsulated in the nanoparticles D1/FITC were both observed around fraction No. 11. From the results, it has been shown that the formation of nanocapsules D1 and the encapsulation of the fluorescent agent FITC into the nanocapsules D1 were achieved.

Example 9

Formation of Fluorescent Agent Encapsulated-Nanoparticles A1/PEG-DY675 (Molecular Probe P1)

In this example, a fluorescent agent PEG-DY675 was encapsulated into nanocapsules A1 formed of the compound (a1) to obtain fluorescent agent-encapsulated nanoparticles A1/PEG-DY675 (molecular probe P1).

The structure of the fluorescent agent PEG-DY675 is shown below.

Scheme 8

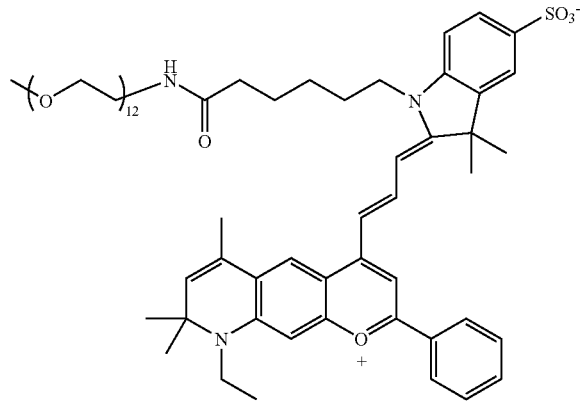

4 mg of the compound (a1) was dissolved in 72 μL of 2,2,2-trifluoroethanol (TFE) to obtain a solution, and the solution was added to 1.5 mL of 10 mM Tris-HCl buffer (pH 7.4) containing 5 mg of PEG-DY675 in an atmosphere having a temperature of 0° C. to form nanoparticles, followed by stirring in an ice bath for 10 minutes, and gel filtration chromatography for purification.

Figure 3:
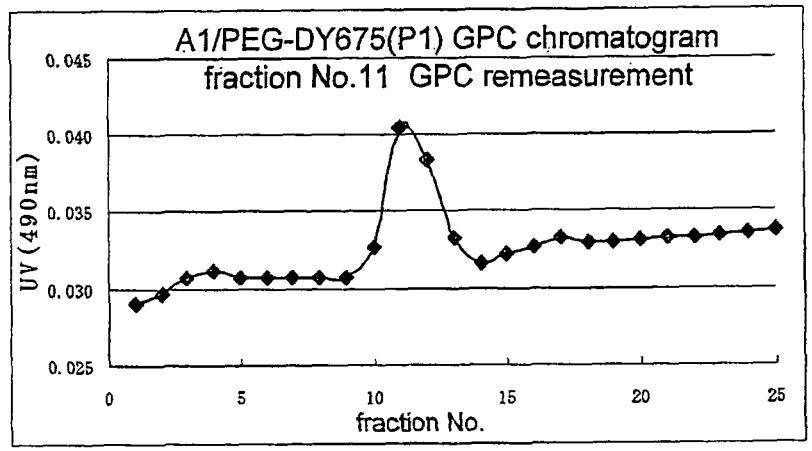
FIG. 3 is a GPC chromatogram of fluorescent agent-encapsulated nanoparticles A1/PEG-DY675 (molecular probe P1) prepared in Example 9.

The nanoparticles were analyzed by gel permeation chromatography. FIG. 3 shows a GPC chromatogram which was obtained by, as in the case of the Example 8, observing the nanocapsule A1 part of the molecular probe P1 near the fraction No. 11, followed by fractionation of the fraction No. 11 and again GPC of the fraction No. 11 using the same column under the same conditions.

Analysis Conditions of A1/PEG-DY675(P1) by GPC
Column Support: Sephacryl S-100 (GE health care)
Eluant: 10 mM Tris-HCl pH 7.4 buffer solution
Amount of Each Fraction: 40 drops/tube
Temperature: 4° C.
Detection Wavelength: 490 nm

Example 10

Formation of Fluorescent Group-Bound Nanoparticles D1-ICG (Molecular Probe P2)

In this example, fluorescent group-bound nanoparticles D1-ICG (molecular probe P2) were formed using the compound d1-ICG. The nanoparticle D1-ICG has a structure in which a fluorescent group ICG is bound to the surface of a nanocapsule D1.

2 mg of d1-ICG was dissolved in 72 μL of 2,2,2-trifluoroethanol (TFE) to obtain a solution, and the solution was injected into 1.5 mL of 10 mM Tris-HCl buffer (pH 7.4) in an atmosphere having a temperature of 0° C. to form nanoparticles, followed by stirring in an ice bath for 10 minutes, and gel filtration chromatography for purification.

Figure 4:
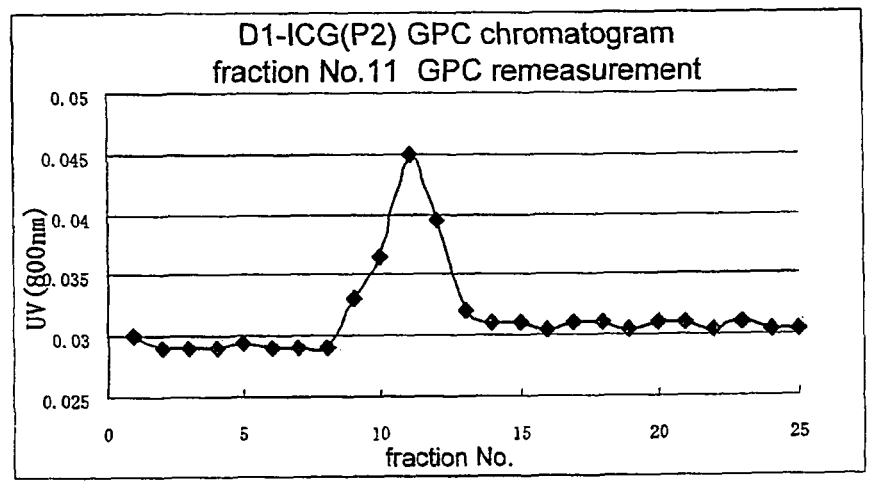
FIG. 4 is a GPC chromatogram of fluorescent group-bound nanoparticles D1-ICG (molecular probe P2) prepared in Example 10.

The nanoparticles were analyzed by gel permeation chromatography. FIG. 4 shows a GPC chromatogram which was obtained by, as in the case of Example 8, observing the nanocapsule D1 part of the molecular probe P2 near the fraction No. 11, followed by fractionation of the fraction No. 11 and again GPC of the fraction No. 11 using the same column under the same conditions.

Analysis Conditions of D1-ICG(P2) by GPC
Column Support: Sephacryl S-100 (GE health care)
Eluant: 10 mM Tris-HCl pH 7.4 buffer solution
Amount of Each Fraction: 40 drops/tube
Temperature: 4° C.
Detection Wavelength: 800 nm From the above, it has been shown that the amphiphilic peptide d1-ICG having the fluorescent group ICG introduced thereinto via chemical bonding formed nanoparticles having a particle size of about 100 nm and that the nanoparticles composed of the nanocapsule D1 having the fluorescent group ICG introduced thereinto were obtained.

Example 11

Test for Examining Stability of Molecular Probe P2 in Blood

The molecular probe P2 was administered into rats (male, 7-week-old), and a change in the plasma level of the molecular probe P2 was observed by fluorometric detection with the lapse of time.

The molecular probe P2 (0.8 mg peptide/mL) was injected into the rat tail vein in an amount of 4 mg/5 mL/kg. After a lapse of 1, 3, 6, 12, 24, 48, 72, and 96 hours from the administration of the molecular probe by injection, about 0.5 mL of blood was sampled from the rat tail vein using a heparin-treated syringe.

Figure 5:
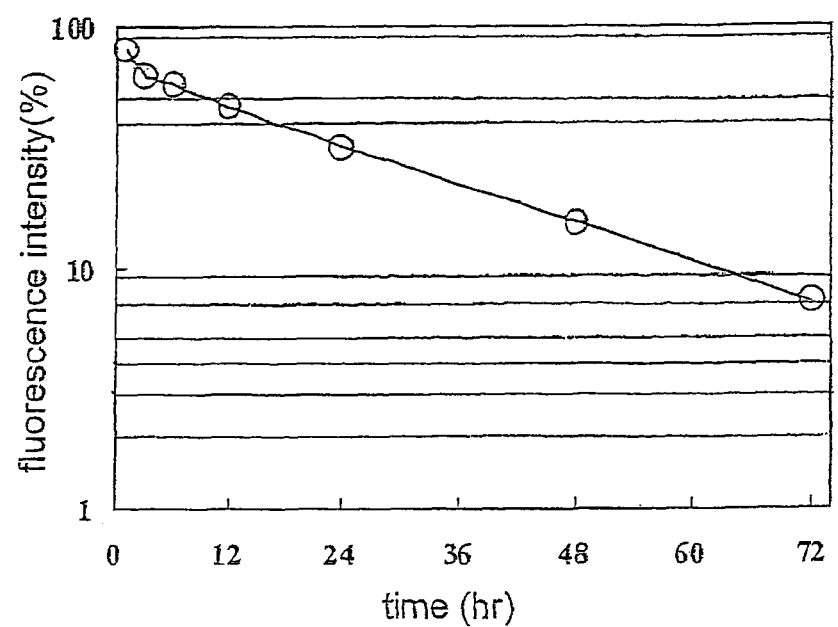
FIG. 5 shows the result of a test for examining the stability of the molecular probe P2 in the blood, carried out in Example 11.

The blood sample was centrifuged (cold microcentrifuge, 10,000 rpm, 10 min, 4° C.) to separate blood plasma, and the fluorescence intensity was measured using a microplate reader (excitation: 678 nm, emission: 807 nm). FIG. 5 shows a change in fluorescence intensity.

As can be seen from FIG. 5, about 50% of the injected dose of the molecular probe P2 was present in a blood vessel even after a lapse of 12 hours from the injection into the blood vessel.

On the other hand, in a case where ICG (indocyanine green) is singly administered, the administered ICG is removed from a body in one hour. Further, according to J Pharmacol Exp Ther. (2004 February; 308(2): 419-425. Epub 2003 Nov. 10.), in a case where 99mTc-BMEDA(N,N-bis(2-mercaptoethyl)-N',N'-diethyl-ethylenediamine) is singly administered as a marker into a body, 90% or more of the administered dose of the 99mTc-BMEDA is removed from the body after a lapse of one hour, and on the other hand, in a case where Doxil®, which is a liposome whose surface has been modified by a polyethylene glycol (PEG) chain labeled with 99mTc-BMEDA, is administered, about 50% of the administered dose of Doxil® is present in a blood vessel after a lapse of about 10 hours.

Therefore, from the result of Example 11, it has been shown that the nanoparticle according to the present invention is equal to the PEG-modified liposome in stability in the blood. That is, the nanoparticles according to the present invention can remain in the blood for a long period of time, which inevitably indicates that the nanoparticles according to the present invention enable accumulation of a drug in a cancer part due to EPR (enhanced permeability and retention) effect.

Example 12

Fluorometric Imaging Test Using Probe P1

Human cancer cells were subcutaneously implanted into mice in the following manner to prepare tumor-bearing mice.

Human cancer cells ($1 \times 10^5$ cells/0.1 mL) were subcutaneously implanted into five- to six-week-old Balb/c nu/nu mice (CREA). The cancer tissue was grown to about 3 to 7 mm after a lapse of 1 week, and the mice were subjected to an imaging test in the following manner.

Each of the tumor-bearing mice was anesthetized with Nembutal, and then 100 μL of a molecular probe dispersion liquid was administered to the mouse through its orbital vein. The fluorescence images of the cancer part and the entire body of the mouse were taken every day for 4 days soon after the administration of the probe dispersion liquid.

In this fluorometric imaging test, the nanoparticles A1/PEG-DY675 (molecular probe P1) synthesized in the Example 9 were used as a molecular probe. The molecular probe P1 is a nanoparticle having DY675 encapsulated therein as a fluorescent agent. As a detection device, ImageQuant™ Imager (GE Healthcare Amersham Bioscience) was used. Fluorescence was excited at 670 nm and measured at 700 nm with the lapse of time.

Figure 6:
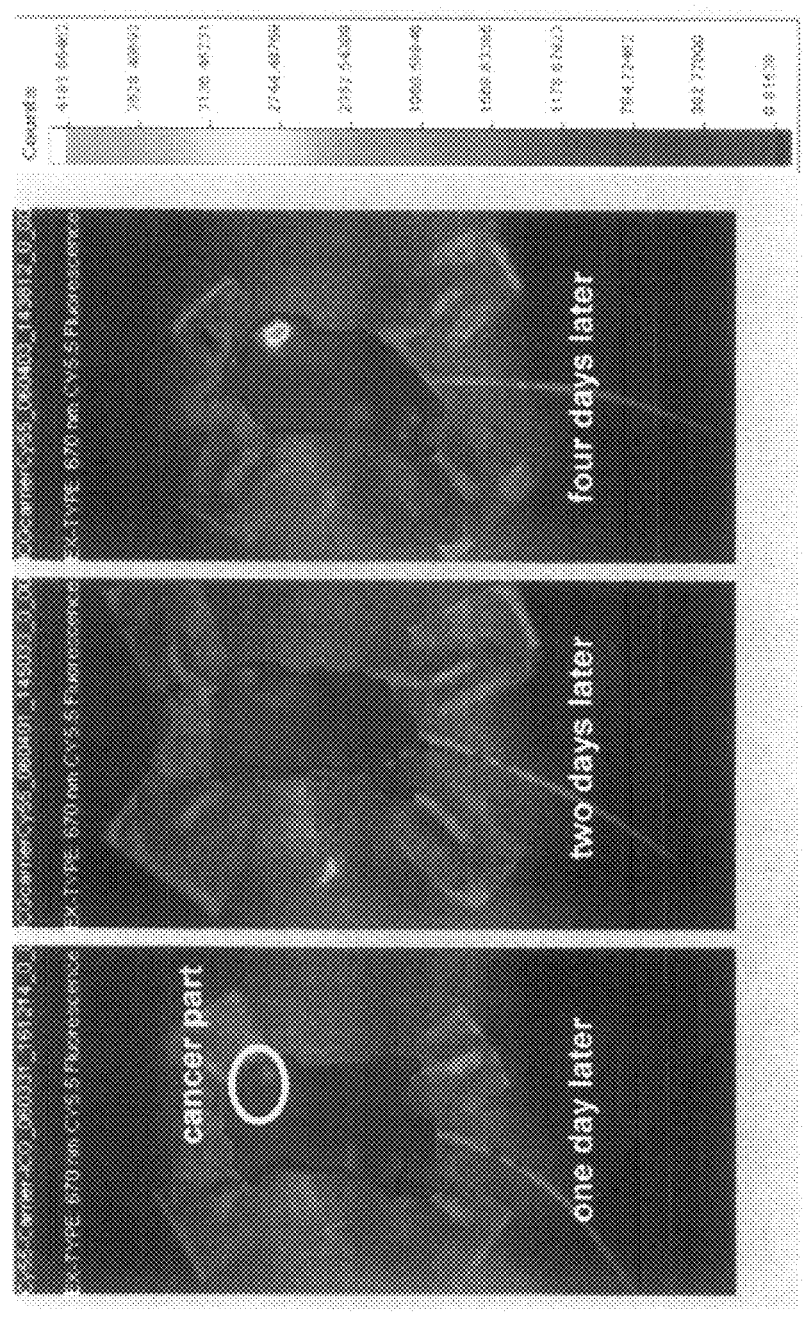
FIG. 6 shows the result of a fluorometric imaging test of a tumor-bearing mouse using the probe P1, carried out in Example 12.

The thus obtained images are shown in FIG. 6. As can be seen from FIG. 6, the molecular probe P1 accumulated in the cancer part, and the accumulation effect of the molecular probe P1 lasted for 4 days.

Example 13

Fluorometric Imaging Test Using Probe P2

A fluorometric imaging test was carried out using a detection device ImageQuant™ Imager in the same manner as in the Example 12 except that the molecular probe was replaced with the nanoparticles D1-ICG (molecular probe P2) synthesized in the Example 10 and that fluorescence was excited at 780 nm and measured at 807 nm with the lapse of time. The molecular probe P2 is a nanoparticle having a fluorescent group ICG bound to the surface thereof.

Figure 7:
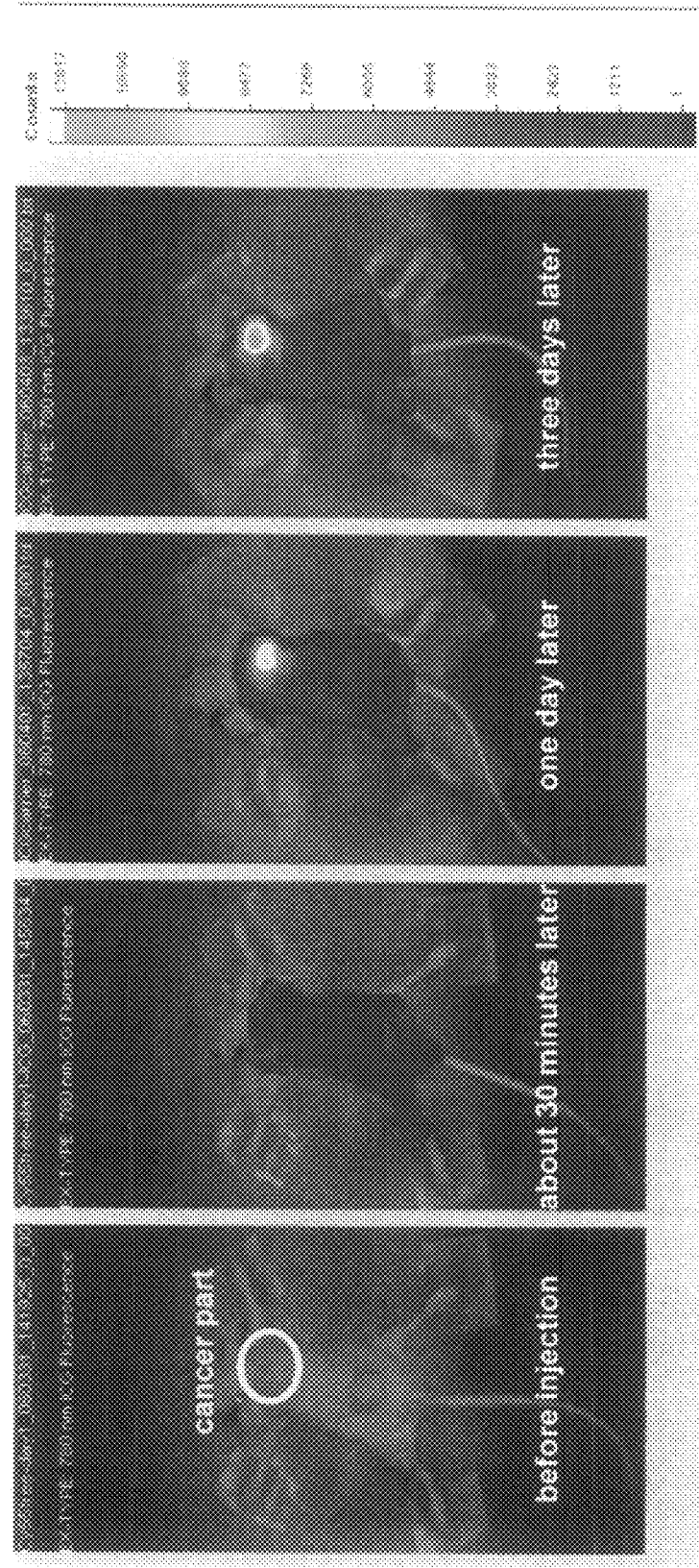
FIG. 7 shows the result of a fluorometric imaging test of a tumor-bearing mouse using the probe P2, carried out in Example 13.

The thus obtained images are shown in FIG. 7. As can be seen from FIG. 7, the molecular probe P2 accumulated in the cancer part, and the accumulation effect of the molecular probe P2 lasted for 3 or more days.

From the results of the Examples 12 and 13, it has been shown that the nanoparticle according to the present invention having a fluorescent agent encapsulated therein and the nanoparticle according to the present invention having a fluorescent group bound to the surface thereof can both accumulate in the cancer part.

The above-described Examples show concrete modes within the scope of the present invention, however, the present invention can be carried out in various other modes. Therefore, the above-described Examples are merely illustrative in all respects, and must not be construed as being restrictive. Further, the changes that fall within the equivalents of the claims are all within the scope of the present invention.

What is claimed is:

1. An amphiphilic block polymer comprising:
   a hydrophilic block; and
   a hydrophobic block, wherein
   the hydrophilic block is a hydrophilic polypeptide chain having 10 or more sarcosine units, and
   the hydrophobic block is a hydrophobic molecular chain comprising units selected from the group consisting of structural units derived from a hydroxyl acid as essential structural units, and having 5 or more of the essential structural units,
   wherein the hydroxyl acid comprises glycolic acid, lactic acid and/or hydroxyisobutyric acid.

2. The amphiphilic block polymer according to claim 1, wherein
   the hydrophobic molecular chain is a hydrophobic polyester chain having 5 or more hydroxyl acid units.

3. The amphiphilic block polymer according to claim 1, further comprising a marker group selected from signal groups and ligands.

4. The amphiphilic block polymer according to claim 3, wherein the marker group is bound to an end of the amphiphilic block polymer.

5. The amphiphilic block polymer according to claim 3, wherein the marker group is bound to the unit constituting the amphiphilic block polymer.

6. A molecular assembly comprising one or more kinds of the amphiphilic block polymers according to claim 1.

7. The molecular assembly according to claim 6, which has a particulate form.

8. The molecular assembly according to claim 7, which is a hollow particle.

9. The molecular assembly according to claim 8, which is a particle having an aqueous phase therein.

10. The molecular assembly according to claim 9, wherein the aqueous phase contains a drug.

11. The molecular assembly according to claim 9, wherein the aqueous phase contains a signal agent and/or a ligand.

12. The molecular assembly according to claim 6, wherein when a marker group is present, the marker group is exposed at the surface of the molecular assembly.

13. The molecular assembly according to claim 6, which has a particle size of 10 to 500 nm.

14. A molecular probe for drug delivery system, comprising the molecular assembly according to claim 10.

15. A drug delivery system comprising administration of the molecular assembly according to claim 10 into a living body.

16. A molecular probe for molecular imaging system, comprising the molecular assembly according to claim 11.

17. A molecular imaging system comprising administration of the molecular assembly according to claim 11 into a living body.

* * * * *